(12) United States Patent
Babu et al.

(10) Patent No.: US 11,364,621 B2
(45) Date of Patent: Jun. 21, 2022

(54) METHOD FOR REGULATING A SAMPLE MANIPULATOR

(71) Applicant: BENDFLEX RESEARCH AND DEVELOPMENT PRIVATE LIMITED, Karnataka (IN)

(72) Inventors: Ramnath T J Babu, Karnataka (IN); Santosh D B Bhargav, Karnataka (IN)

(73) Assignee: BENDFLEX RESEARCH AND DEVELOPMENT PRIVATE LIMITED, Karnataka (IN)

( * ) Notice: Subject to any disclaimer, the term of this patent is extended or adjusted under 35 U.S.C. 154(b) by 372 days.

(21) Appl. No.: 16/475,141

(22) PCT Filed: Aug. 8, 2017

(86) PCT No.: PCT/IN2017/050328
§ 371 (c)(1),
(2) Date: Jul. 1, 2019

(87) PCT Pub. No.: WO2018/122863
PCT Pub. Date: Jul. 5, 2018

(65) Prior Publication Data
US 2019/0329401 A1    Oct. 31, 2019

(30) Foreign Application Priority Data
Dec. 31, 2016    (IN) .............................. 201641045190

(51) Int. Cl.
*B25J 7/00*     (2006.01)
*G01N 1/28*     (2006.01)
*G01N 1/04*     (2006.01)
*B25J 15/12*    (2006.01)
*B25J 9/16*     (2006.01)

(52) U.S. Cl.
CPC ............... *B25J 7/00* (2013.01); *B25J 9/1612* (2013.01); *B25J 15/12* (2013.01); *G01N 1/04* (2013.01); *G01N 1/286* (2013.01)

(58) Field of Classification Search
None
See application file for complete search history.

(56) References Cited

U.S. PATENT DOCUMENTS

| | | | | |
|---|---|---|---|---|
| 5,278,776 A * | 1/1994 | Fisher | .................. | A61B 5/0055 600/587 |
| 10,126,219 B2 * | 11/2018 | Shabram | .................. | G01N 3/08 |
| 2014/0147028 A1 * | 5/2014 | Zheng | .................. | G06T 7/0014 382/131 |
| 2014/0257569 A1 * | 9/2014 | Yip | ........................ | G05B 15/02 700/275 |

FOREIGN PATENT DOCUMENTS

KR    101294250    *    8/2013

* cited by examiner

*Primary Examiner* — Daniel S Larkin
(74) *Attorney, Agent, or Firm* — Mark M. Friedman (57) ABSTRACT

The invention provides a method for regulation of a sample manipulator. The method includes generating a list of at least one first displacement for at least one pre-defined object; estimating a least one second displacement with respect to at least one location on the manipulator; comparing the estimated displacement with the list of first displacements to obtain an optimum displacement; and computing at least one second force at the given location from the obtained optimum displacement. The estimation of the optimum displacement facilitates regulation of the manipulator.

11 Claims, 8 Drawing Sheets

METHOD FOR REGULATING A SAMPLE MANIPULATOR

FIELD OF INVENTION

The invention generally relates to the field of biomedical engineering and particularly to a method for estimating force and regulating a manipulator for manipulation of sample.

BACKGROUND

Holding of a sample and subsequent manipulation, by isolating the sample from a given environment has numerous medical and scientific applications. Examples of manipulation include a task that includes but is not limited to squeezing, gripping, grasping, rolling, stretching, bending, piercing, probing and tearing. Examples of samples include but are not limited to biological cells, tissues, scaffolds, tissue-scaffolds, biopsies, zygotes, organelles, platelets, sand-particles, amorphous, crystals and crystalline structures. Various manipulators have been designed for gripping samples.

Each of the manipulation stated herein above requires precise handling of the manipulator. Manipulators can be rigid, elastic or partially resilient. It is important to estimate the force generated by the manipulator in order to determine the force required for a certain manipulation. Method of force estimation can be classified into intrusive method or non-intrusive method. Intrusive method of estimation of force includes but is not limited to introduction of force sensors on the manipulator. One significant disadvantage of the method is the bulkiness of the apparatus due to presence of sensors. Another disadvantage is that the introducing sensors could affect that values being estimated. Further, the use of external sensors is permissible if the locations of displacement of the manipulator are known. Examples of non intrusive method of force estimation include but are not limited to visual method. The method of estimating force on the manipulator is a visual method wherein displacements or derivatives of displacements such as stress or strain suffered by actuation of the manipulator are utilized in estimation of the force.

One such known visual method provides computation of forces acting on the boundary or the interior of a constrained elastic body using visually measured displacement data at selected points. The method involves partitioning of the elastic body into two regions a domain where displacements are measured and a measurement free region. The method also defines a boundary with constraints. The domain and the boundary are utilized in estimation of forces. However, one significant disadvantage of the method is that the method is computationally intensive and not-suitable for real-time estimation. Also, the method provides an indirect measurement of the force. Hence, there is a need for a method that is simple to perform and is independent of method to measure the displacement.

BRIEF DESCRIPTION OF DRAWINGS

So that the manner in which the recited features of the invention can be understood in detail, some of the embodiments are illustrated in the appended drawings. It is to be noted, however, that the appended drawings illustrate only typical embodiments of this invention and are therefore not to be considered limiting of its scope, for the invention may admit to other equally effective embodiments.

FIGS. 4 (a) and (b) shows a graph of computed displacements for determination of force for manipulation, according to an example of the invention.

FIGS. 5 (a) and (b) shows a graph of computed displacements for determination of force for manipulation, according to an example of the invention.

SUMMARY OF THE INVENTION

One aspect of the invention provides a method for regulation of a sample manipulator. The method includes generating a list of at least one first displacement for at least one pre-defined object. A first force is estimated for the first displacement. At least one second displacement is estimated with respect to at least one location on the manipulator; comparing the estimated displacement with the list of first displacements to obtain an optimum displacement; and computing at least one second force at the given location from the obtained optimum displacement. The estimation of the optimum displacement facilitates regulation of the manipulator.

DETAILED DESCRIPTION OF THE INVENTION

Various embodiments of the invention provide a method for regulation of a sample manipulator. The method includes generating a list of at least one first displacement or its derivative for at least one pre-defined object; estimating a least one second displacement with respect to at least one location on the manipulator; comparing the estimated displacement with the list of first displacements to obtain an optimum displacement; and computing at least one second force at the given location from the obtained optimum displacement. The estimation of the optimum displacement facilitates regulation of the manipulator. Each of the steps mentioned in brief hereinabove shall be explained in detail.

Figure 1:
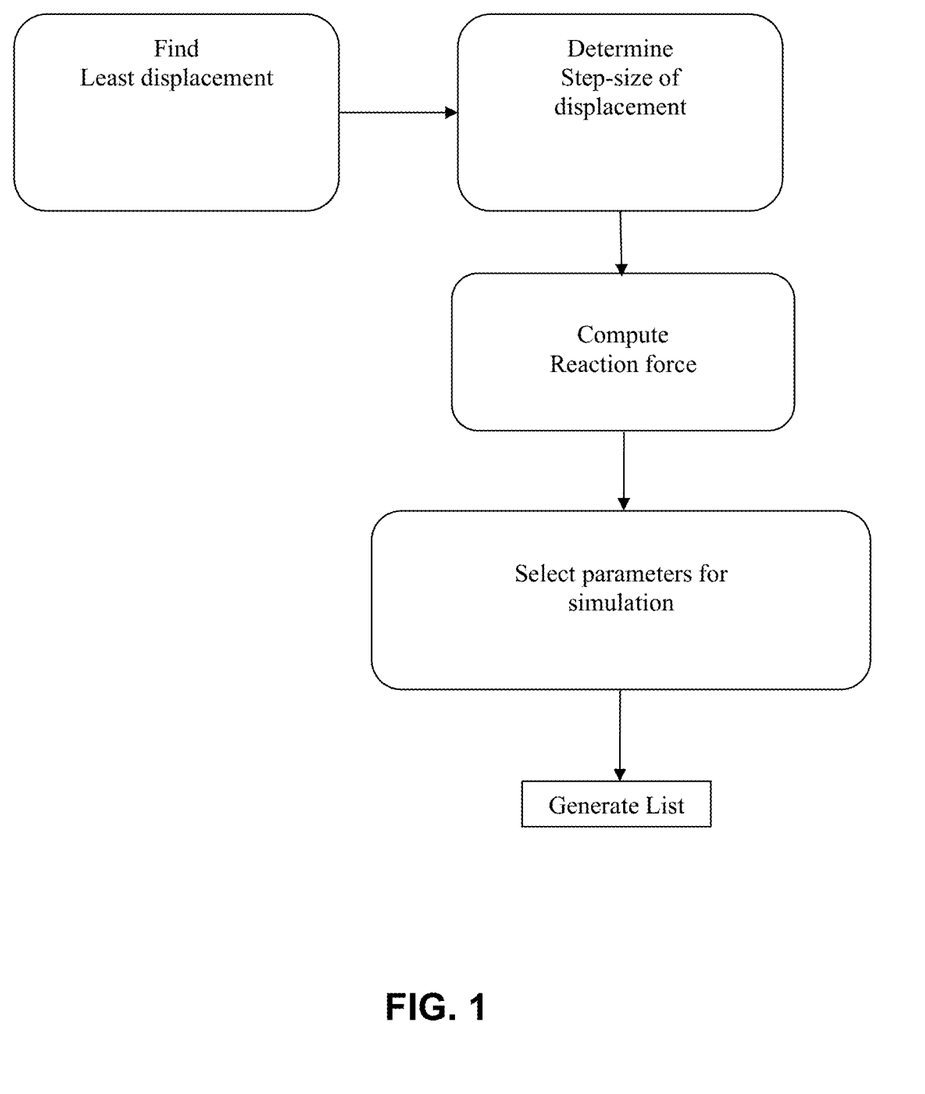
FIG. 1 shows a flowchart of obtaining a reference list, according to an embodiment of the invention.

FIG. 1 shows a flowchart of obtaining a reference list, according to an embodiment of the invention. The method of obtaining the reference list includes the step of estimating a least displacement of the manipulator for manipulation of a pre-defined object. The predefined object can be any object of any given geometry that has a defined means of manipulation. The manipulation is a task performed by the manipulator. Examples of task include but are not limited to squeezing, gripping, grasping, rolling, stretching, bending, piercing, probing, tearing or a combination thereof.

Figure 4:
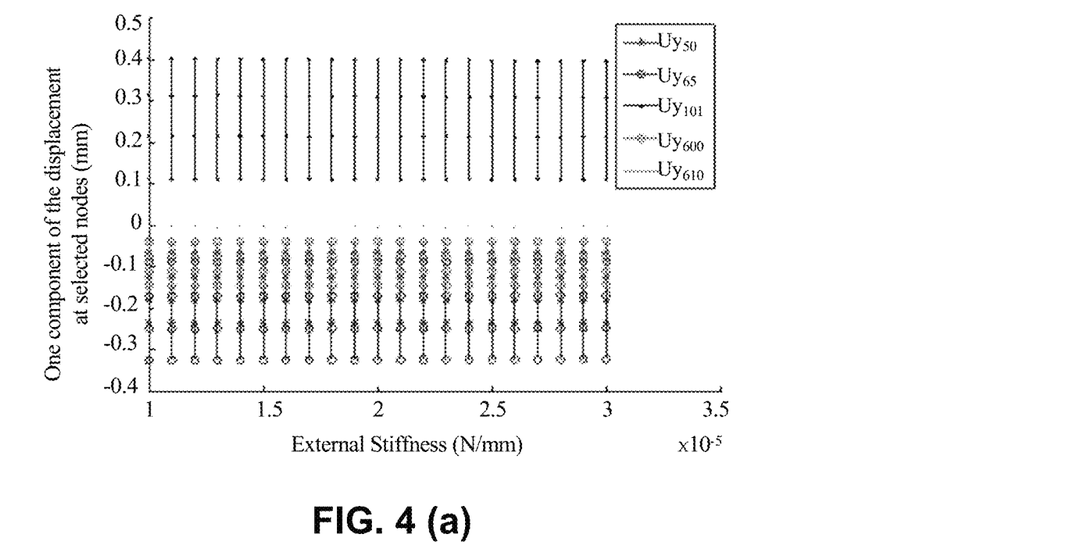
Figure 5:
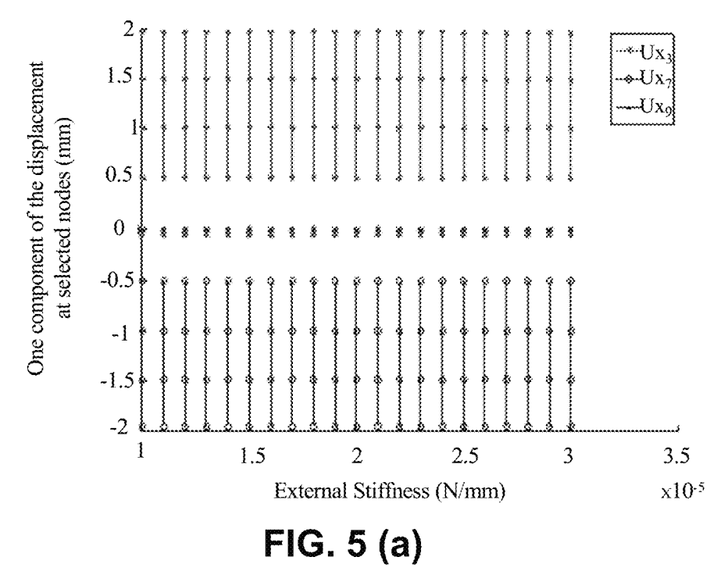

In one example of the invention, the image of an object whose dimensions are known, say a ruler edge, is taken using the camera. Then the smallest displacement that can be measured is computed by taking the ratio of the actual dimension of the object to the number of pixels along that dimension of the object in the digital image. Subsequent to determination of the least displacement, a step-size for the estimated displacement is determined. A first force required for suffering the said least displacement is computed. In one example of the invention, the ratio of the computed force to the applied displacement gives the smallest stiffness that can be resolved. The step size of displacement and the force corresponding to each of the displacement computed are then subjected to a simulation. In one example a finite element analysis is adopted as a means for simulation. Other examples of simulation include but are not limited to decision tree algorithm; support vector machines, SVM; genetic algorithms; and all such algorithms capable of obtaining a list through iterative processing, as obvious to a person skilled in the art. During the simulation, the step size is incremented to compute a plurality of forces wherein the incremental computation of forces yields the list. Examples of list generated include but are not limited to a graph, a table or a combination thereof. FIG. 4 and FIG. 5 shows a graph of computed displacements for determination of force for manipulation, according an embodiment of the invention.

Figure 2:
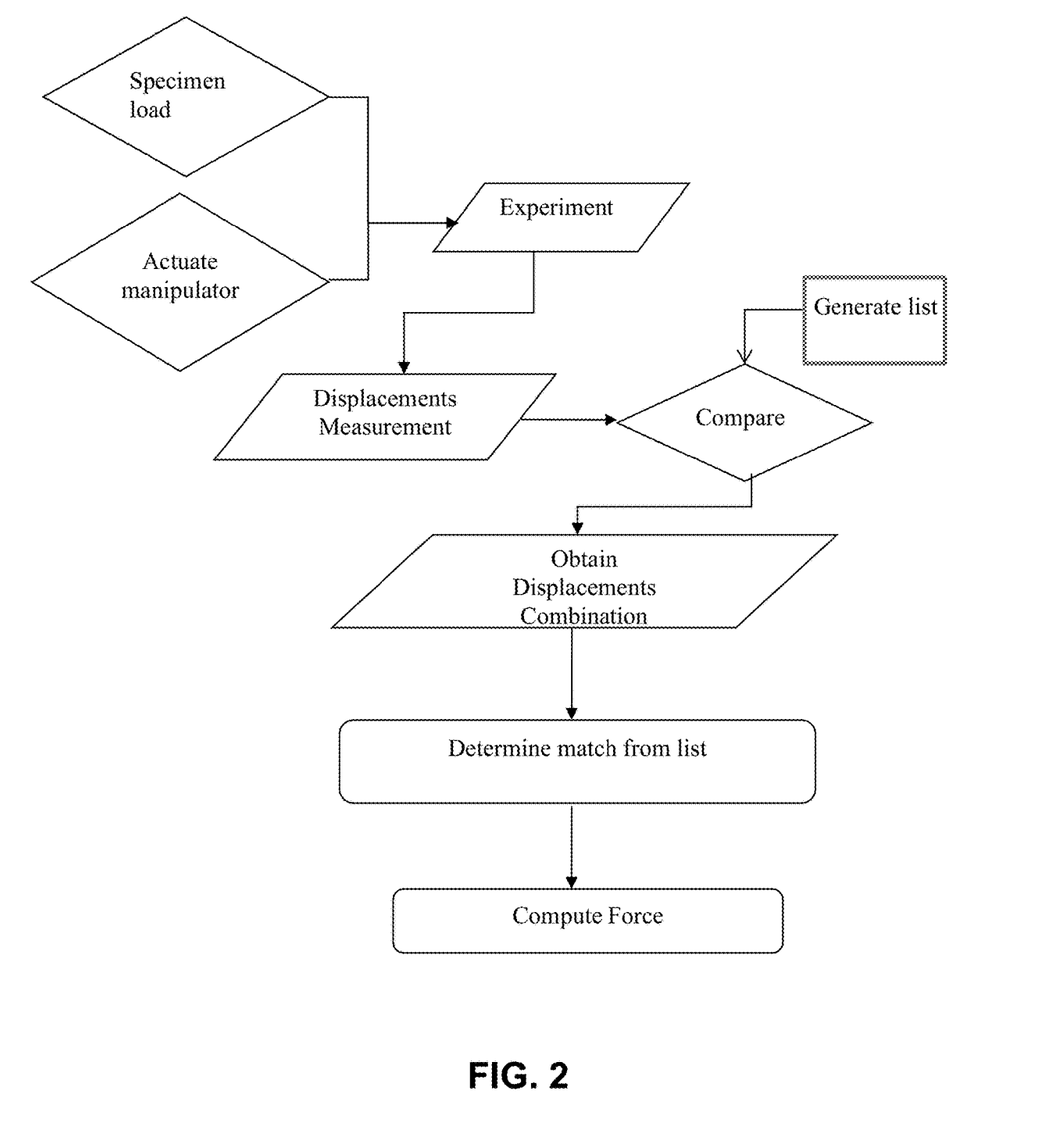
FIG. 2 shows a flowchart of the method of force estimation, according to an embodiment of the invention.

The list generated through the method as described hereinabove is then utilized for determining force required to perform a defined manipulation on a sample, by the manipulator. FIG. 2 shows a flowchart of the method of force estimation, according to an embodiment of the invention. Examples of sample include but are not limited to biological cells, tissues, scaffolds, tissue-scaffolds, biopsies, zygotes, organelles, platelets, sand-particles, crystals and crystalline structures. The sample is loaded onto the manipulator and a predefined task is performed, to achieve a manipulation. The displacements suffered by the manipulator at various locations are noted. In one example of the invention, a marker is introduced at various locations on the manipulator. Examples of markers include but are not limited to spots, dots, through-cuts, corners, protrusions, embossing, fillets, patches, sintered or any other form of creating regions that can be marked on the frame of the manipulator and as obvious to a person skilled in the art. The displacements measured from one or more of the locations on the manipulator are then compared with the table. The values of the forces, stiffness value of the specimen and the displacements at other locations are retrieved from the table. If combination of the displacements does not correspond to the values in a particular row in the table, then the closest combination that depicts the actual displacement is chosen designating more weightage to the displacement of the actuation point. This displacement is the optimum displacement which is then utilized for computation of second force. The second force is the actuation force on the manipulator. Based on the second force estimated, the operation of the manipulator can be regulated.

The force that is estimated by the method as described herein above can also be utilized to develop a sample manipulator with a regulated force that the manipulator applies on to the specimen. The above objective can be achieved by performing at least one of the following that includes but is not limited to a) modifying the geometric proportions including the in-plane width, length of the members, out-of-plane thickness; b) changing the material of the sample manipulator, either wholly or at selected locations on the manipulator; or a combination thereof.

Figure 3:
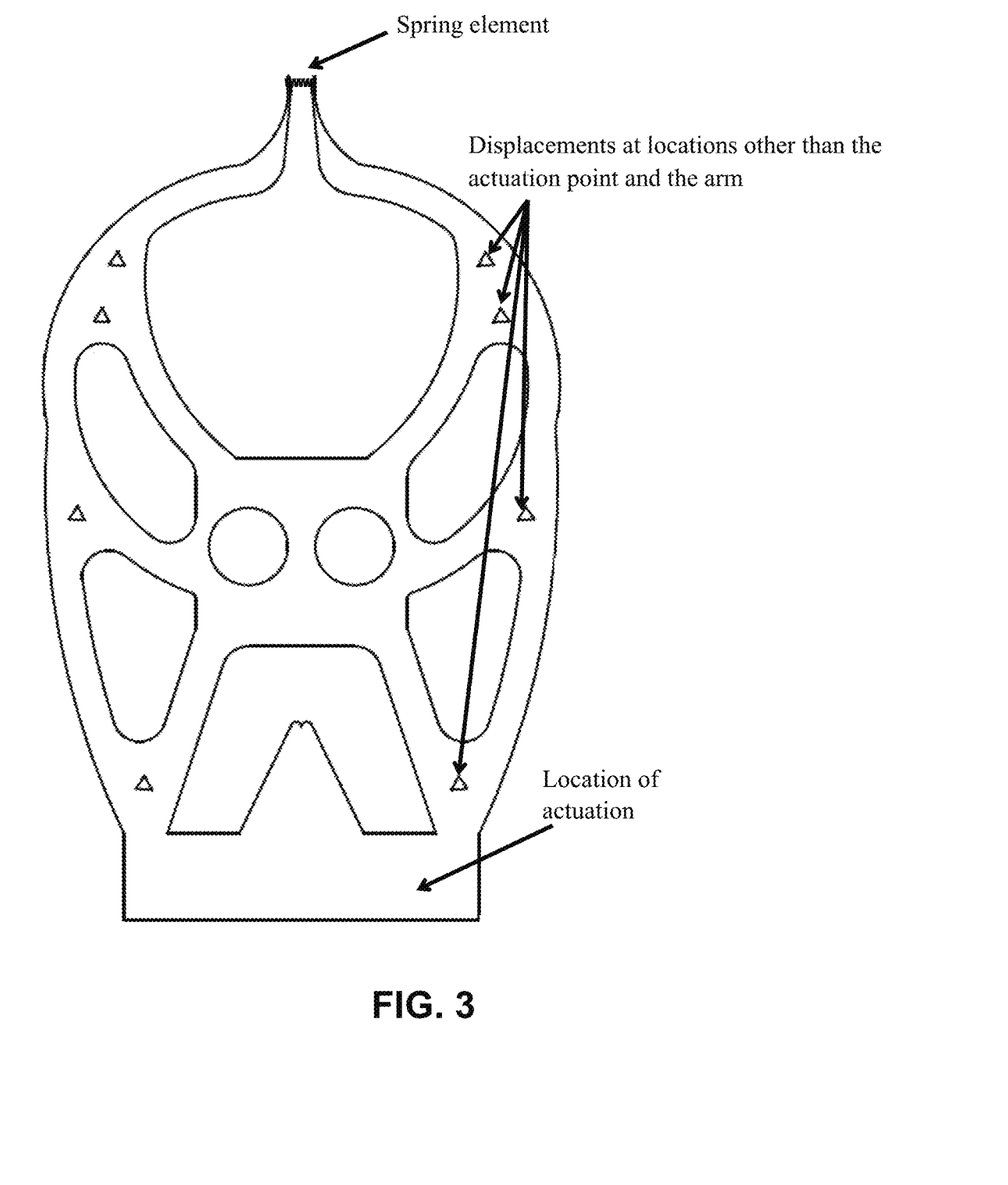
FIG. 3 shows a representative manipulator with a spring held between the arms, according to one example of the invention.
Figure 6A:
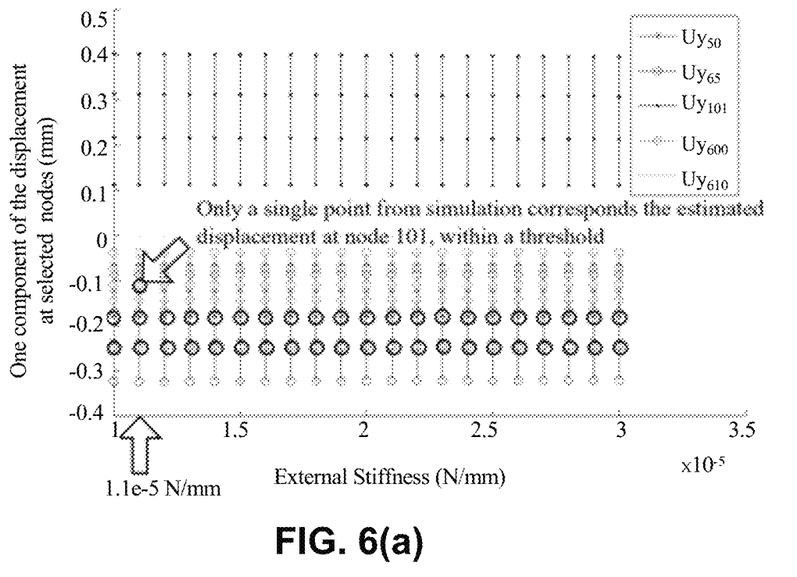
FIGS. 6a and 6b show a graph of computed displacements for determination of force for manipulation, according to an example of the invention.

Example 1: Estimation of force: The method as described herein above is adopted for estimation of force on a given object. In one specific example of the invention, the object is a spring. FIG. 3 shows a representative manipulator with a spring held between the arms, according to one example of the invention. Example of spring includes but is not limited to a torsion spring, a compression spring. The objective is to estimate the Force required for performing a squeezing action on the spring. Initially, the displacement on the manipulator at a pre-defined location on the manipulator is estimated. The location can be a designated position on the manipulator or a plurality of positions on the manipulator. The displacements obtained are then compared with the list generated as shown in FIG. 4. The comparison with the list can be achieved either manually or electronically. The comparison yields an optimum value of displacement that corresponds to a specimen stiffness of $1.1e^{-5}$ N/mm as shown in FIG. 6a. The optimum value of displacement obtained is then utilized to determine the force of manipulating the object. The force determined is about 0.615 µN.

Figure 6B:
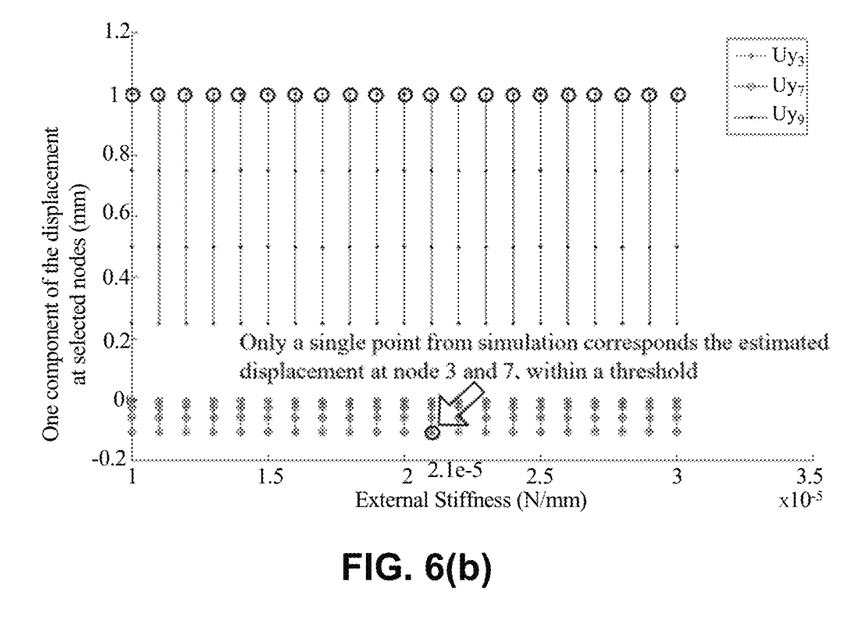

The method as described herein above is adopted for estimation of force required for extension of the spring, by a manipulator. In one specific example of the invention, the object is a spring. Examples of springs includes but are not limited to a torsion spring, a compression spring. Initially, the displacement on the manipulator at a pre-defined location on the manipulator is estimated. The location can be a designate position on the manipulator or a plurality of positions on the manipulator. The displacements obtained are then compared with the list generated as shown in FIG. 5. The comparison with the list can be achieved either manually or electronically. The comparison yields an optimum value of displacement that corresponds to a specimen stiffness of $2.1e^{-5}$ N/mm as shown in FIG. 6b. The optimum value of displacement obtained is then utilized to determine the force of manipulating the object. The force determined is about 83.7 µN.

In another embodiment of the invention, the list of displacements obtained in respect of pre-defined objects is also utilized for determining stiffness of the manipulator of the application.

Example 1 is a case wherein the regulation is brought about using the design, before the experiment begins.

Example 2: Stiffness tuning: As an example, it is important to ensure that the force or deformation applied by the manipulator on a soft object like a single biological cell is not exceeding a value beyond which it will damage the object of concern object. While the force that the manipulator applies on the specimen can be estimated by the aforementioned method, one can also estimate the deformation using the first list of displacement that we generate as a part of the aforementioned method. This regulation of the force either through estimation of force or through the first list of displacement is achieved by designing the frame to have a particular stiffness depending on the stiffness of the object that is being manipulated. There is scope to develop a frame of desired stiffness by choosing an appropriate combination of choice of the material, the in-plane width, out-of-plane thickness, length of the members of the mechanism and anchoring points. For example, for a particular scenario of manipulating an oocyte will impose a restriction that the material used has to be bio-compatible.

Figure 7:
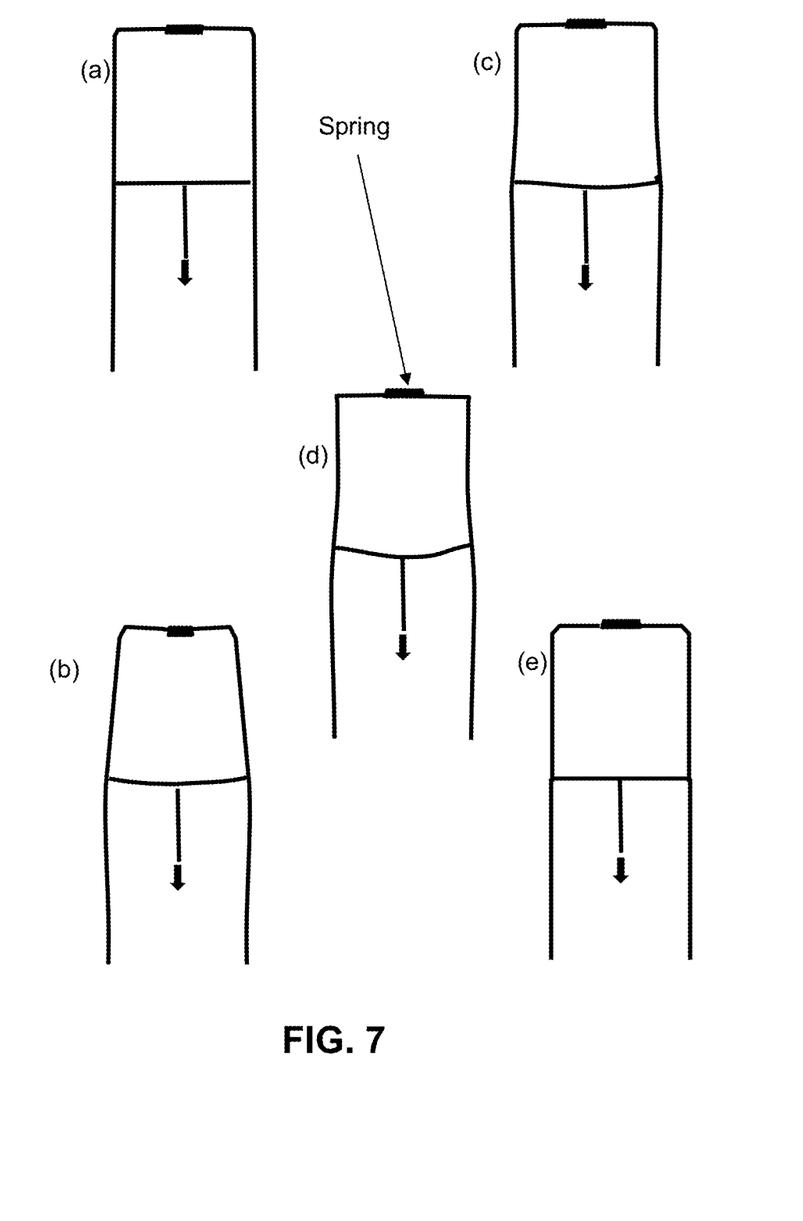
FIG. 7 generally depicts the modification of stiffness based on various parameters, according to one example of the invention.
Figure 8:
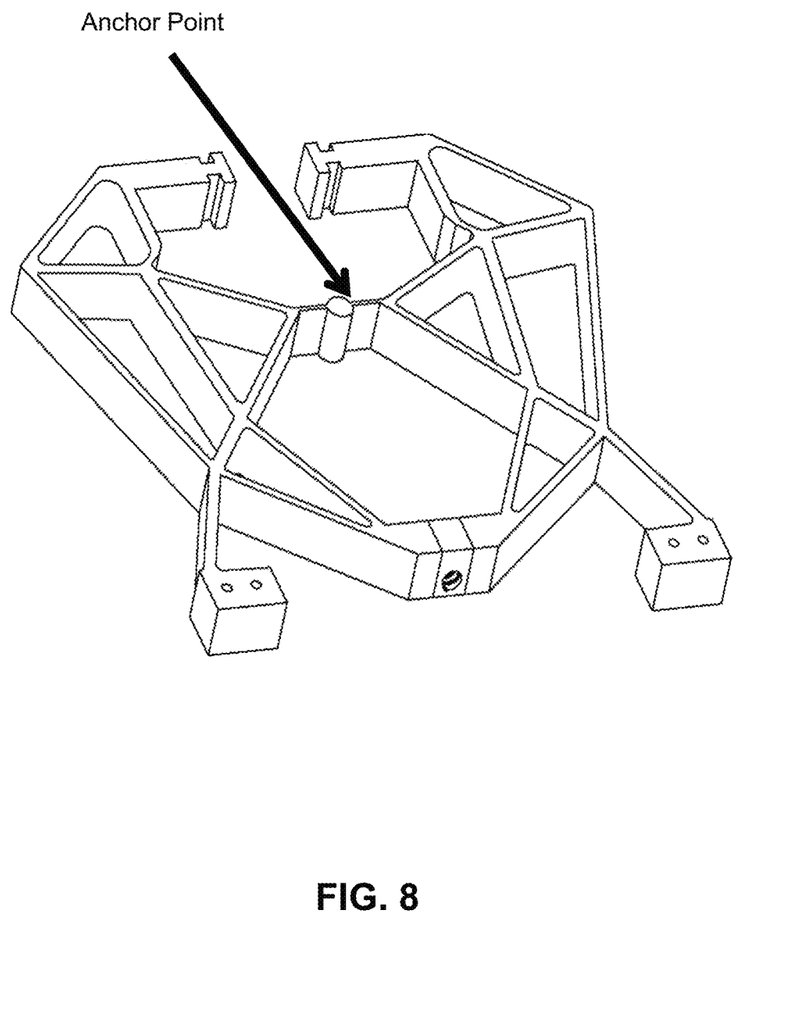
FIG. 8 depicts the point of introduction of an additional anchoring point in a manipulator, according to an alternate embodiment of the invention.

Upon selection of the material and the associated material properties, the out-of-plane thickness of the material is determined. It is noted that the manipulator can be a single piece even though it has a more than one materials. One possible means of achieving this is using through additive manufacturing like 3D-printing. The out-of-plane thickness of the frame is limited by the size of the specimen that needs manipulation. If the out-of-plane thickness of the mechanism is more than the specimen size then the arms shall occlude the object and cast a shadow, which is not desirable especially in cases where the experiment takes place under a microscope, thereby introducing a restriction on the length of the arms of the manipulator. Therefore, stiffness can be tuned by varying at least one of the remaining parameters: in-plane width, length of the members and altering the anchoring points. FIG. 7 generally depicts the modification of stiffness based on various parameters, according to one example of the invention. The mechanism comprises of beams that have a uniform rectangular cross-section of 1.2 mm×1.2 mm and have an average length of about 16.42 mm. Further a spring is attached at the 'jaws' of the frame as shown in FIG. 7(a). The spring has a stiffness of 0.01 N/mm. The resilient frame when subjected to a displacement of 0.2 mm at its input point, as shown in FIG. 7 (a), deforms the spring. The deformation is represented in FIG. 7 (b). It can be observed in FIG. 7(b) that the spring gets deformed substantially to about 0.8 mm. Now, there could be a case where the stiffness of the spring in itself more than the stiffness at the resilient frame. FIG. 7(c) is one such case where the frame depicted in FIG. 7(a) tries to deform a/an specimen/object having a spring-constant of 0.3 N/mm. Alternatively, the cross-section parameters of the beams can be reduced to reduce the stiffness of the frame and thereby apply only a limited load/deformation on the spring having a spring-constant of 0.01 N/mm. FIG. 7(d) is a particular case where the cross-section is reduced to 0.5 mm×0.5 mm, and the stiffness of the frame is reduced to an extent that now it can deform the spring of 0.01 N/mm by about 0.1 mm. There is yet another way of tuning the stiffness of the frame by introducing non-proportional changes in the beam parameters. The non-proportional changes includes but not limited to a simultaneous change in one or more of the cross-section, length of the beam-segments, different materials at one or more places, varying out-of-plane thickness, FIG. 7 (e) is a particular example where the cross-sections are varied such that a few regions have a cross-section of 1.2 mm×1.2 mm while others have a cross-section of 0.5 mm×0.5 mm. In this case the frame is capable of deforming the spring of 0.01 N/mm by about 0.5 mm when it actuated by about 0.2 mm. While retaining the topology of the frame one could make proportional and non-proportional changes in its members to achieve a wide range of stiffness to control the amount of load that is applied on to the specimen. FIG. 8 depicts the point of introduction of an additional anchoring point in a manipulator, according to an alternate embodiment of the invention. The introduction of the additional anchor point increases the in-plane stiffness and increases the out-of-plane stiffness. However, one may also design such that reduces the in-plane stiffness and out-of-plane stiffness. Such an anchor point could be brought about by having a surface wherein the establishing contact there will enable the constraint. Also, the constraint could also be a sliding or rolling or rotation or a combination of these. Example 2 is a case wherein the regulation happens after the design and while the experiment is in progress.

The invention provides a method for regulation of a sample manipulator through estimation of various parameters including but not limited to actuation force, displacement, altering at least one of the dimensions of the manipulator, the material of the manipulator or a combination thereof. The method can be advantageously used either manually or electronically to efficiently manipulate a given object. The method can also be used to design manipulators suitable for a particular manipulation of a particular object.

The foregoing description of the invention has been set merely to illustrate the invention and is not intended to be limiting. Since modifications of the disclosed embodiments incorporating the spirit and substance of the invention may occur to person skilled in the art, the invention should be construed to include everything within the scope of the appended claims and equivalents thereof.

We claim:

1. A method for regulation of a sample manipulator, the method comprising of:
    generating a list of first displacements for at least one pre-defined object, measured on at least one location on the at least one predefined object by:
        estimating a least displacement of the manipulator for manipulation of the at least one pre-defined object,
        determining a step-size for the estimated displacement,
        obtaining a first force required for the said least displacement, and
        incrementing the step size to compute a plurality of forces, wherein the incremental computation of forces yields the list;
    estimating second displacements with respect to at least one location on the manipulator, wherein a sample is loaded onto the manipulator and a predefined task is performed to achieve a manipulation wherein said second displacements of the manipulator at various locations are noted;
    comparing the estimated second displacements with the list of first displacements to obtain a value; and
    computing at least one second force at a given location from the obtained value, said at least one second force being used for regulation of the sample manipulator.

2. The method of claim 1, wherein the value is equal to, greater than or lesser than a threshold value wherein the threshold value is the closest displacement obtained from the list.

3. The method of claim 1, wherein the first force is a reaction force.

4. The method of claim 1, wherein the at least one second force is the force required for manipulation of the sample.

5. The method of claim 1, wherein the list is a graph, a table or a combination thereof.

6. The method of claim 1, wherein the at least one pre-defined object is an object having a known manipulation.

7. The method of claim 1, wherein the at least one pre-defined object has at least one pre-determined mechanical property.

8. The method of claim 7, wherein the at least one mechanical property has a pre-defined range of values associated with the property.

9. The method of claim 1, wherein the manipulation is a task, the task selected from a list comprising of squeezing, gripping, grasping, rolling, stretching, bending, piercing, probing, tearing or a combination thereof.

10. The method of claim 1, wherein the sample is selected from a list comprising of biological cells, tissues, scaffolds, tissue-scaffolds, biopsies, zygotes, organelles, platelets, sand-particles, crystals and crystalline structures.

11. The method of claim 1, further wherein the first displacement enables altering at least one of the dimensions of the manipulator, the material of the manipulator or a combination thereof.

* * * * *